United States Patent
Gupta et al.

(10) Patent No.: US 11,350,990 B2
(45) Date of Patent: Jun. 7, 2022

(54) FLEXIBLE CIRCUIT HAVING IMPROVED ADHESION TO A RENAL NERVE MODULATION BALLOON

(71) Applicant: BOSTON SCIENTIFIC SCIMED, INC., Maple Grove, MN (US)

(72) Inventors: Ajay Gupta, Minneapolis, MN (US); Jeffrey S. Lindquist, Maple Grove, MN (US); Paul J. Miller, Vadnais Heights, MN (US); Cass A. Hanson, St. Paul, MN (US); Daniel T. Quillin, Eden Prairie, MN (US); Hong Cao, Maple Grove, MN (US); Kenneth R. Larson, Grand Rapids, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 16/902,751

(22) Filed: Jun. 16, 2020

(65) Prior Publication Data
US 2020/0305973 A1    Oct. 1, 2020

Related U.S. Application Data

(63) Continuation of application No. 14/465,597, filed on Aug. 21, 2014, now Pat. No. 10,722,300.
(Continued)

(51) Int. Cl.
*A61B 18/14* (2006.01)
*B32B 37/12* (2006.01)
(Continued)

(52) U.S. Cl.
CPC ...... *A61B 18/1492* (2013.01); *B32B 37/1292* (2013.01); *A61B 2017/00526* (2013.01);
(Continued)

(58) Field of Classification Search
CPC ...... A61B 18/1492; A61B 2017/00526; A61B 2018/00214; A61B 2018/0022;
(Continued)

(56) References Cited

U.S. PATENT DOCUMENTS

2005/0137615 A1 *   6/2005   Mapes ........... A61B 17/320725
                                                          606/159
2008/0319350 A1 * 12/2008   Wallace ................. A61B 5/053
                                                          600/587
(Continued)

*Primary Examiner* — Tigist S Demie
(74) *Attorney, Agent, or Firm* — Seager, Tufte & Wickhem, LLP (57) ABSTRACT

A balloon for renal nerve modulation is disclosed. The balloon may include a polymer material forming a balloon wall having an outer surface and flexible circuits comprising a base selectively adhered to the exterior surface of the balloon wall. Adhesive is selectively applied to the outer surface of the balloon, to the flexible circuit or to both such that the adhesive is selectively deposited on the at least a portion of the at least two pads or on the at least a portion of the at least two pads and to a portion of the distal spline. The portion of the at least two pads or the portion of the at least two pads and a portion of the distal spline are adhered to the outer surface of the balloon and a remainder of the flexible circuit moves freely with respect to the outer surface of the balloon.

20 Claims, 7 Drawing Sheets

Related U.S. Application Data (60) Provisional application No. 61/868,863, filed on Aug. 22, 2013.

(51) Int. Cl.
*A61B 18/00* (2006.01)
*A61B 17/00* (2006.01)

(52) U.S. Cl.
CPC .............. *A61B 2018/0022* (2013.01); *A61B 2018/00214* (2013.01); *A61B 2018/00404* (2013.01); *A61B 2018/00434* (2013.01); *A61B 2018/00511* (2013.01); *A61B 2018/00577* (2013.01); *A61B 2018/00714* (2013.01); *A61B 2018/00797* (2013.01); *A61B 2018/00815* (2013.01); *A61B 2018/1465* (2013.01); *A61B 2018/1467* (2013.01); *Y10T 156/10* (2015.01)

(58) Field of Classification Search
CPC ........... A61B 2018/00404; A61B 2018/00434; A61B 2018/00511; A61B 2018/00577; A61B 2018/00714; A61B 2018/00797; A61B 2018/00815; A61B 2018/1465; A61B 2018/1467; B32B 37/1292; Y10T 156/10

See application file for complete search history.

(56) References Cited

U.S. PATENT DOCUMENTS

| | | | |
|---|---|---|---|
| 2009/0014120 A1* | 1/2009 | Konrath | H05K 3/321 156/291 |
| 2012/0158101 A1* | 6/2012 | Stone | A61F 7/12 607/101 |
| 2014/0128859 A1* | 5/2014 | Lee | A61L 29/14 606/33 |

* cited by examiner

FLEXIBLE CIRCUIT HAVING IMPROVED ADHESION TO A RENAL NERVE MODULATION BALLOON

CROSS-REFERENCE TO RELATED APPLICATIONS

This application is a continuation of Ser. No. 14/465,597, filed Aug. 21, 2014 and granted on Jul. 28, 2020 as U.S. Pat. No. 10,722,300, which claims priority under 35 U.S.C. § 119 to U.S. Provisional Application Ser. No. 61/868,863, filed Aug. 22, 2013, the entirety of which is incorporated herein by reference.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

In one aspect, the present disclosure relates to a balloon for renal nerve modulation, the balloon comprising a polymer material forming a balloon wall having an inner surface and an outer surface and flexible circuits comprising a base formed of a polymer material are selectively adhered to the exterior surface of the balloon wall, the base of each of the flexible circuit comprises a distal pad and a proximal pad and a distal spline connecting the at least two pads, adhesive is selectively applied to the outer surface of the balloon, to the flexible circuit or to both such that the adhesive is selectively deposited on the at least a portion of the at least two pads or on the at least a portion of the at least two pads and to a portion of the distal spline, wherein the portion of the at least two pads or the portion of the at least two pads and a portion of the distal spline are adhered to the outer surface of the balloon and a remainder of the flexible circuit moves freely with respect to the outer surface of the balloon.

In another aspect, the present disclosure relates to a method of making a renal denvervation balloon, the method comprising providing a preformed balloon, the balloon comprising a body portion, waist and cone portions, providing at least two flexible circuits, the base of each flexible circuit comprising at least two pads and a distal spline, applying adhesive selectively to an outer surface of the balloon, the at least two flexible circuits, or to both such that the base of each of the flexible circuit that contacts the outer surface of the balloon at a portion of the at least two pads or at a portion of the at least two pads and a portion of the distal spline is adhered to the balloon and a remainder of the flexible circuit moves freely with respect to the outer surface of the balloon.

These and other aspects, embodiments and advantages of the present disclosure will become immediately apparent to those of ordinary skill in the art upon review of the Detailed Description and Claims to follow.

DETAILED DESCRIPTION

While embodiments of the present disclosure may take many forms, there are described in detail herein specific embodiments of the present disclosure. This description is an exemplification of the principles of the present disclosure and is not intended to limit the disclosure to the particular embodiments illustrated.

The present disclosure is directed to devices for percutaneous renal artery denervation, particularly expandable balloons and to methods of making and using the same.

Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Deactivation of nerves in the kidneys via renal artery denervation can reduce blood pressure, and may be a viable treatment option for many patients with hypertension who do not respond to conventional drugs.

Ultrasound, radiofrequency energy, microwave energy, direct heating elements, and balloons with heat or energy sources may be applied to a region of sympathetic nerves.

A specific method for treatment of the renal sympathetic nerves involves a percutaneous, catheter-based therapy that uses radiofrequency energy to disrupt the renal sympathetic nerves. This method involves the use of an expandable medical balloon which is advanced to the treatment site, expanded, and energy is transmitted through the balloon via flexible circuits disposed on the outside of the balloon.

The flexible circuits are bonded to the outside surface of the renal denervation balloon.

Delamination of the flexible circuits during balloon insertion, refolding and withdrawal can be an issue. There remains a need in the art for improved balloons for renal artery denervation having high robustness.

The present disclosure relates to balloon for renal nerve modulation comprising a balloon wall having an interior and an exterior surface and flex circuits adhesively bonded to the exterior of a balloon. Renal nerve modulation or renal denervation is sometimes used to treat conditions relating to hypertension and/or congestive heart failure.

While the devices and methods disclosed herein are discussed relative to renal nerve modulation, it is contemplated that these devices and methods may be employed in other treatments as well.

The devices and methods according to the disclosure involve the delivery of radiofrequency energy to the renal nerve permanently modify nerve function.

Treatment involves delivery of the balloon to a treatment site via a catheter delivery device, inflation of the balloon at the treatment site, delivery of energy to the flexible circuit for nerve denervation, deflation and refolding of the balloon, and pulling of the balloon back into the catheter delivery device for withdrawal from the patient.

In alternative embodiments, other sources of energy such as ultrasound energy, microwave energy or direct heating elements may be employed for renal artery denervation.

Figure 1:
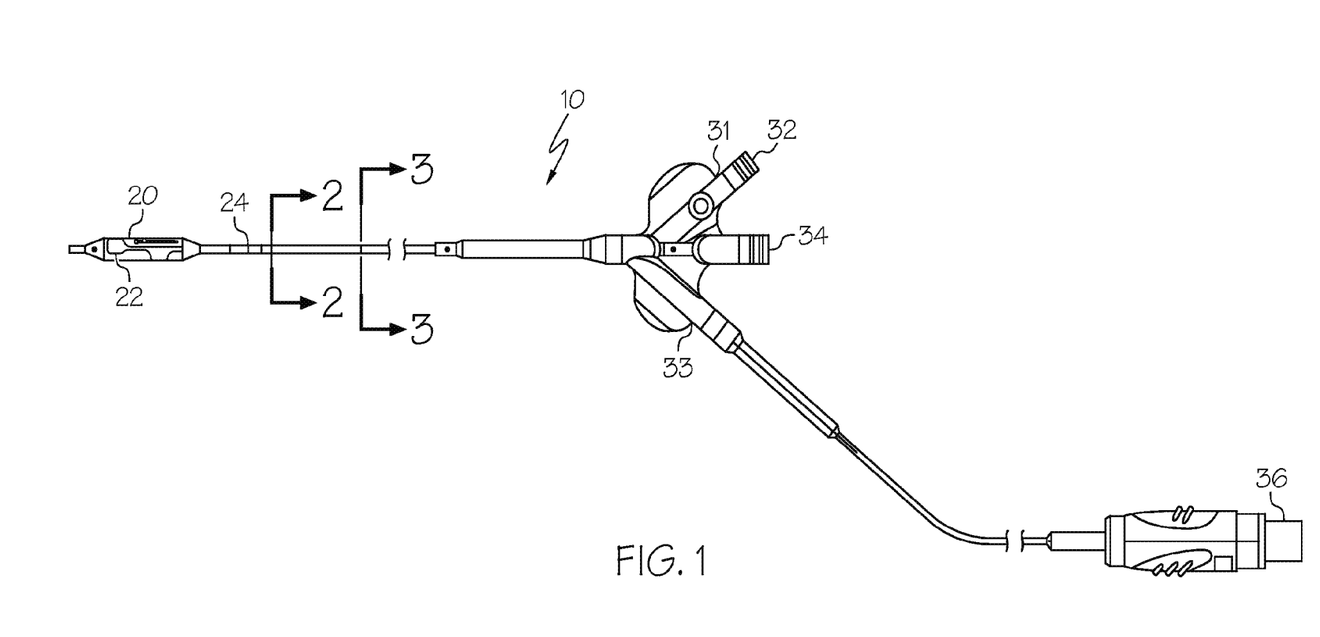
FIG. 1 is a side view of a catheter having a renal nerve modulation balloon according to the disclosure disposed on the distal end thereof.

Turning now the drawings, FIG. 1 is a side view of a catheter or catheter assembly 10 having a balloon 20 for renal nerve modulation disposed at the distal end thereof. Catheter 10 includes a manifold 31 having a port 32 for inflation fluid, a port 33 through which wires run from the electrodes on the flexible circuits 22 to the electric plug 36 to a generator (not shown), and a guidewire lumen 34.

Figure 6:
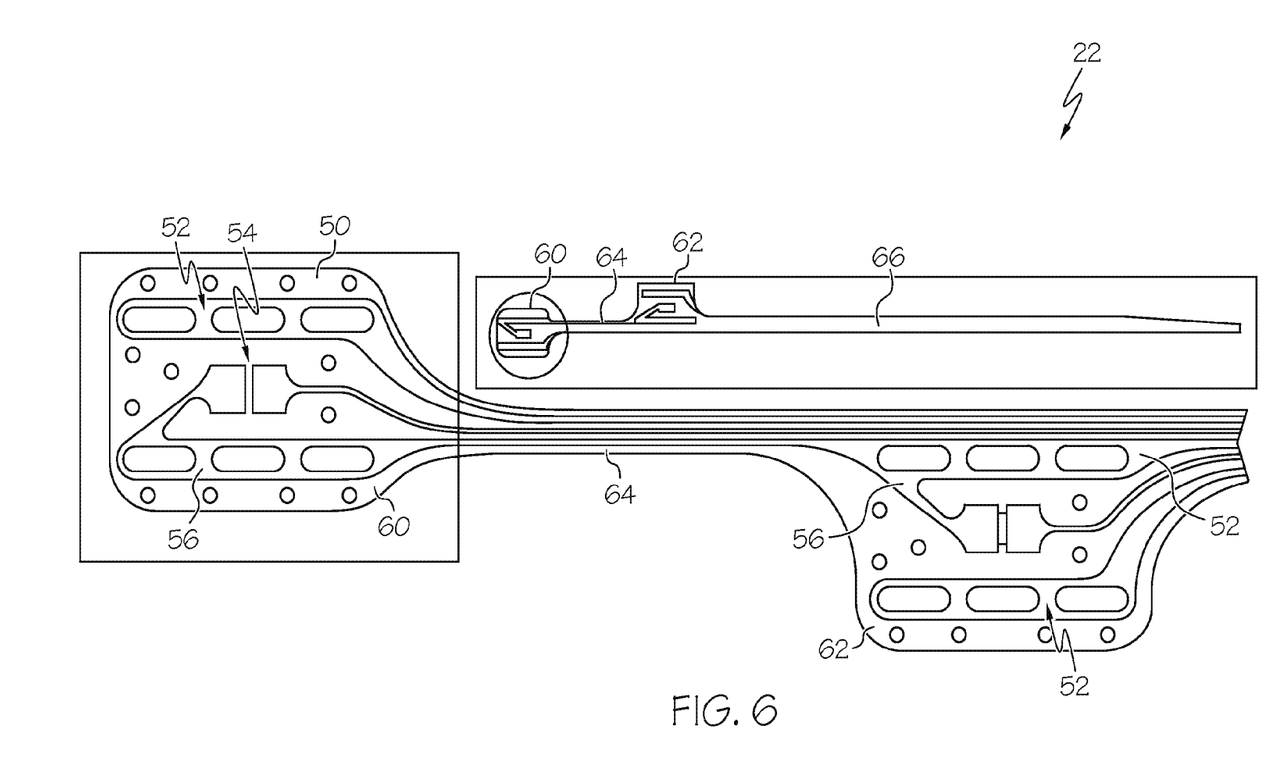
FIG. 6 illustrates one embodiment of a flexible circuit for use on the renal nerve modulation balloon.

Balloon 20 includes flexible circuits 22 disposed thereon. Balloon 20 is a radially expandable balloon. Balloon 20 is delivered to a treatment site in a patient's vasculature and inflated with fluid supplied through port 32 during use. The balloon is bonded at the distal end to the distal end of an outer catheter shaft 24 and at the proximal end to an inner catheter shaft. Each flexible circuit, explained in more detail with respect to FIG. 6 is formed of a base polymer material 50 comprising two pads 60, 62, each of which contains two pairs of electrodes connected to a power supply at the proximal end of the device via wires disposed within the outer catheter shaft.

The flexible circuit is formed from a relatively rigid polymeric material with copper pathways for conducting current between the electrodes.

Figure 2:
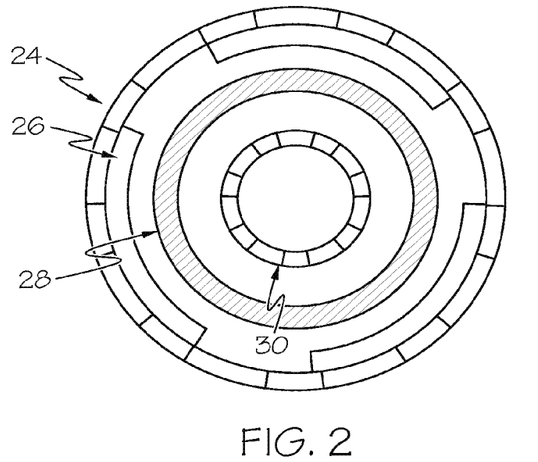
FIG. 2 is a radial cross-section taken at section 2-2 in FIG. 1.

FIG. 2 is a cross-sectional view taken at section 2-2 in FIG. 1 illustrating the outer shaft 24 of catheter 10, electrodes 26 disposed within outer shaft 24, inflation lumen 28 and guidewire lumen 30. While electrodes 26 are show disposed within outer shaft 24, in other embodiments electrodes 26 may be disposed along an outer surface of outer shaft 24.

Figure 3:
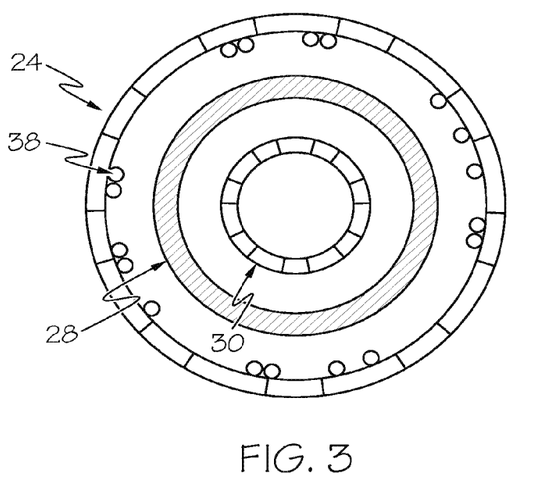
FIG. 3 is a radial cross-section taken at section 3-3 in FIG. 1.
Figure 4:
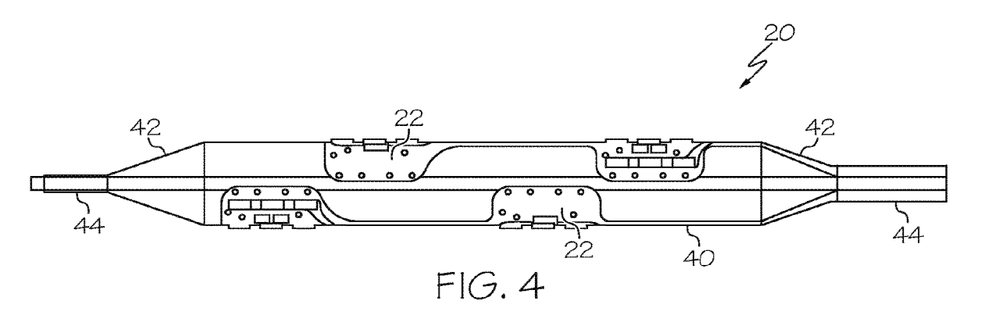
FIG. 4 is a side view of an embodiment of a renal nerve modulation balloon having flexible circuits disposed thereon.

FIG. 3 is a radial cross-sectional view taken at section 3-3 in FIG. 1 further illustrating wires 38 at are distally coupled to electrodes 26. These wires provide power and grounds for the temperature sensors and ablation electrodes. FIG. 4 is a side view of one embodiment of a balloon 20 for renal nerve modulation illustrating two flexible circuits 22 disposed therein. FIG. 4 is illustrative of a balloon that is 4 mm in diameter. Balloon 20 includes a body portion 40, a proximal cone portion 42, a proximal waist portion 44, a distal cone portion 43 and a distal waist portion 45.

Figure 5:
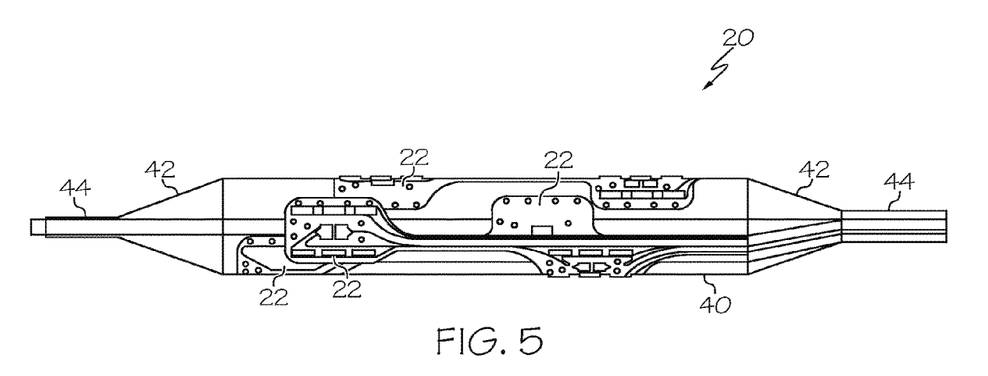
FIG. 5 is a side view of another embodiment of a renal nerve modulation balloon having flexible circuits disposed thereon.

FIG. 5 is a side view of one embodiment of a balloon 20 for renal nerve modulation illustrating four flexible circuits 22 disposed thereon. Alternatively, balloon 20 may have 3, 5 or more flexible circuits disposed thereon.

Larger balloons of 5, 6, 7 or 8 mm diameter, may include a larger number of flexible circuits such as 3 or more flexible circuits.

In this embodiment, each flexible circuit is formed from a polymer base material 50. Polymer base material 50 may include a polyimide material such as Kapton® polyimide available from DuPont™ in Wilmington, Del.

The composite nature of the flexible circuit results in a relatively rigid structure compared the polymeric balloon which can hinder the balloon from refolding efficiently upon deflation prior to being pulled back into the guide catheter. This can further result in high shear and buckling forces during re-entry into the guide catheter and over bends through the tortuous body lumen of the renal artery, for example.

In this embodiment, the flexible circuit is defined by two pads 60, 62 connected by a distal spline portion 64. Proximal spline portion 66 extends from pad 62 to nearly the proximal waist portion of the balloon (see FIG. 1) wherein wires 38 (see FIGS. 2 and 3) are soldered thereto. Wires 38 then run through port 33 to the plug 36 for a generator (not shown in FIG. 1).

Each flexible circuit, as illustrated in FIG. 6, has two electrode pairs 52, coupled to a thermistor 54 mounted on copper traces for individual temperature control feedback, and a shared ground 56. In this embodiment, electrodes 52 are formed from gold but can be formed from any suitable material such as platinum, stainless steel, cobalt alloys, and other non-oxidizing materials. Each flexible circuit forms a complete bipolar circuit which is beneficial because there are reduced treatment variation effects from non-targeted body tissue proximity such as fatty tissue, or energy loss due to variations in blood flow cooling effects.

The flexible circuit further includes copper wires which may be lithographically printed thereon.

In this embodiment, the electrodes are spatially arranged for 360° circumferential coverage and spaced longitudinally with an offset about the balloon resulting in coverage of the artery that avoids ablating a single circumferential ring which might cause injury to healthy renal tissue, potentially resulting in vessel trauma and stenosis. Thus, the discrete treatment locations provided by the individual flexible circuits 22 are spatially arranged to provide full circumferential coverage of the vessel for denervation while minimizing negative impact to the healthy vessel.

The balloon may be formed of noncompliant polymer materials or semi-compliant or compliant polymer materials.

Compliant balloons are made from relatively soft or flexible polymeric materials. Examples of these materials are thermoplastic polymers, thermoplastic elastomers, polyethylene (high density, low density, intermediate density, linear low density), various copolymers and blends of polyethylene, ionomers, polyesters, polyurethanes, polycarbonates, polyamides, polyvinyl chloride or acrylonitrile-butadiene-styrene copolymers. A suitable copolymer material, polyolefin material is available from E. I. DuPont de Nemours and Co. (Wilmington, Del.), under the trade name Surlyn® Ionomer.

Intermediate compliant balloons are made of polyether-block-amide (PEBA) copolymers and nylon materials.

Non-compliant balloons are made from relatively rigid or stiff polymeric materials. These materials are thermoplastic polymers and thermoset polymeric materials. Some examples of such materials are poly(ethylene terephthalate), polyimide, thermoplastic polyimide, polyamides, polyesters, polycarbonates, polyphenylene sulfides, polypropylene and rigid polyurethanes. Non-Compliant balloons made from poly(ethylene terephthalate) are commonly referred to as PET balloons.

In some embodiments, the balloon is formed of a non-compliant polymer material such as polyethylene terephthalate (PET).

The flexible circuit 22 is disposed on the outer surface of the balloon 20. Suitably, the flexible circuit 22 is disposed on the balloon 20 surface via an adhesive bond.

Adhesive is applied selectively either to the flexible circuit 22 or to balloon 20 wherein the inner surface of the base polymer material 50 meets the outer surface of a balloon 20. It has been found that stress on the circuit can be reduced by selectively placing adhesive on base 50 of the flexible circuit 22 thereby reducing undesirable failure modes between the balloon and the flexible circuit during refolding and withdrawal.

Withdrawal forces can be relatively high, for example, about 2 lbs. These high withdrawal forces can cause partial or full delamination of the flexible circuit from the balloon.

Selective placement of the adhesive on the flexible circuit allowing portions of the flexible circuits 22 to move freely by design thereby relieving stress on the system and to enable the balloon to refold more efficiently during insertion, refolding and withdrawal. Reducing withdrawal force helps to prevent uncontrolled delamination of the flexible circuit from the balloon.

FIGS. 7-12 are flat views of the inner surface of the flexible circuits, e.g., the surface of that is applied to the balloon, illustrating various embodiments of adhesive selectively disposed thereon.

Figure 7:
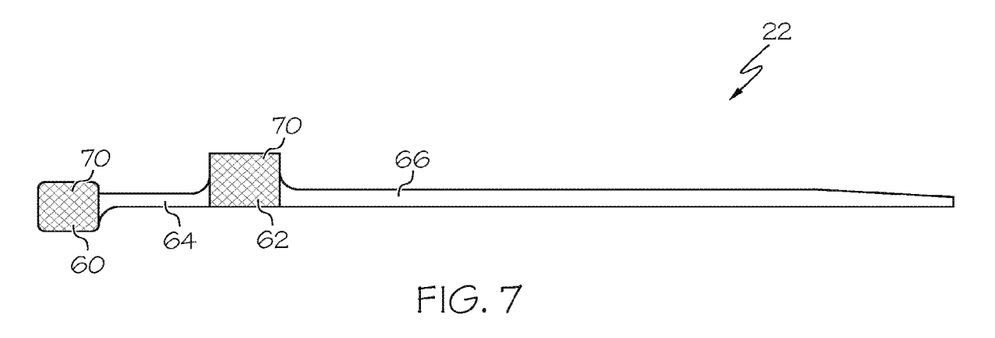
FIGS. 7-12 are flat views of the inner surface of the flexible circuits, e.g., the surface of that is applied to the balloon, illustrating various embodiments of adhesive selectively disposed thereon.

FIG. 7 illustrates an embodiment wherein each of the distal and proximal pads 60, 62 comprises adhesive 70 selectively disposed thereon. It has been found that providing the pads 60, 62 maintain relative positions with respect to each other, the space between the two electrodes remains fixed, and optimal ablation spacing is maintained.

Figure 8:
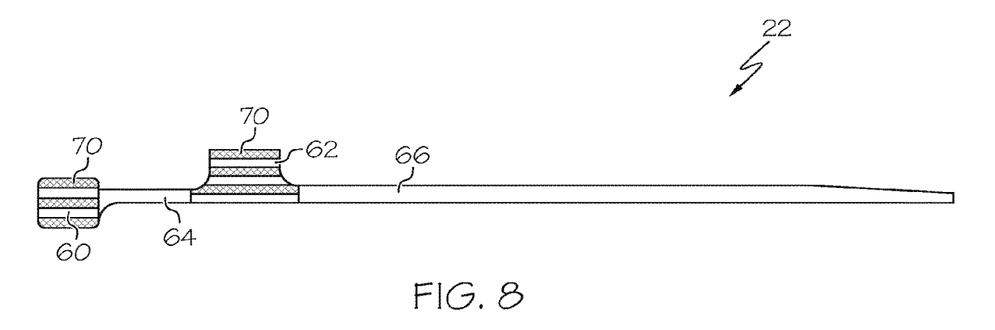

FIG. 8 illustrates an alternative embodiment wherein each of the distal and proximal pads 60, 62 comprises stripes of longitudinal adhesive 70 that run parallel with the longitudinal axis of the flexible circuit 22.

Figure 9:
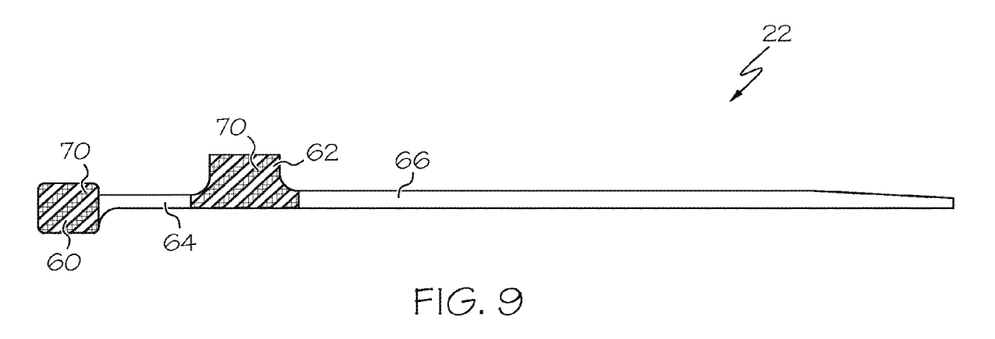

FIG. 9 illustrates an alternative embodiment wherein the adhesive 70 is applied to each of the distal and proximal pads 60, 62 in stripes that run diagonally to the longitudinal axis of the catheter assembly.

Figure 10:
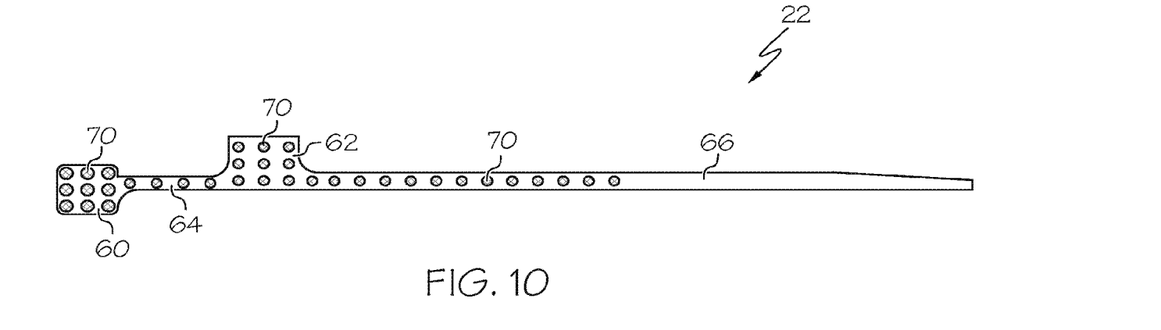
Figure 11:
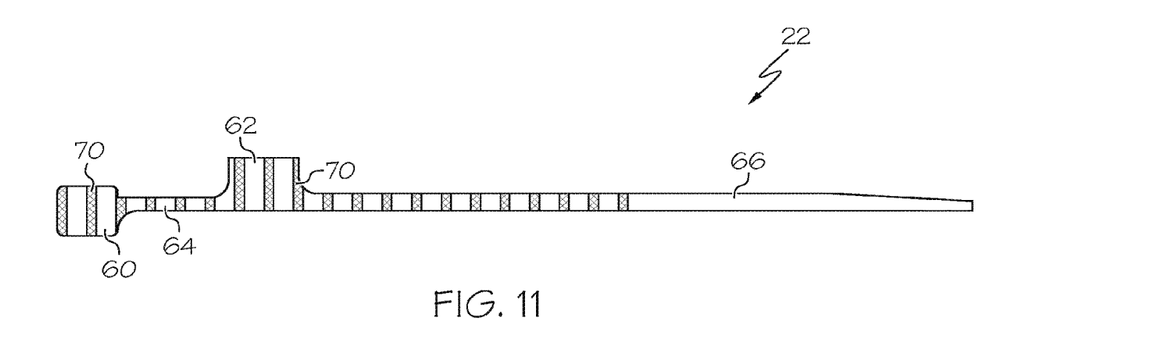
Figure 12:
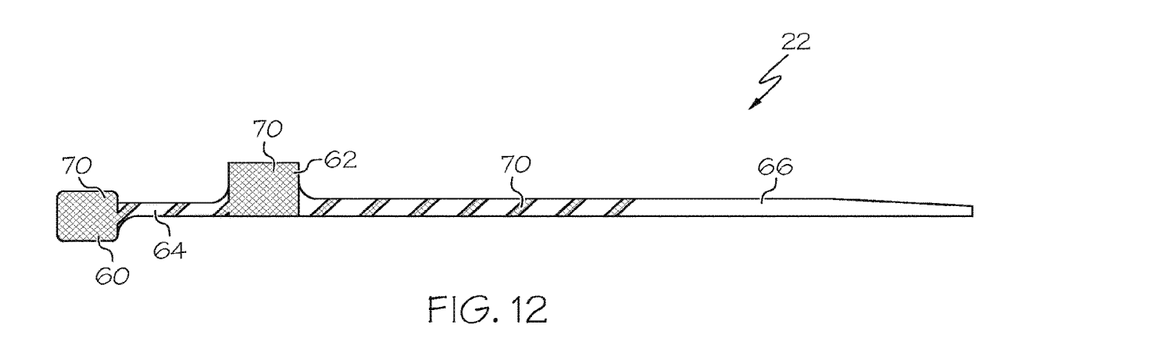

In alternative embodiments as shown in FIGS. 10-12, adhesive 70 is also selectively applied to the distal spline 64 and the proximal spline 66.

In FIG. 10, dots of adhesive 70 are applied in a uniform pattern on each of the distal and proximal pads 60, 62 and on both the distal spline 64 and the proximal spline 66.

FIG. 11 illustrates an embodiment wherein adhesive 70 is applied in stripes that run perpendicularly to the longitudinal axis of the catheter assembly. Adhesive 70 is applied to the distal and proximal pads 60, 62 as well as to the distal and proximal spline portions 64, 66.

FIG. 12 is an alternative embodiment wherein adhesive 70 is applied to the full surfaces of the distal and proximal pads 60, 62 and is applied in uniform diagonal stripes to the distal and proximal spline 64, 66.

The above embodiments are for illustrative purposes only and are not intended to limit the scope of the present disclosure. The adhesive can be applied in numerous other patterns and shapes without deviating from the scope of the present disclosure.

Any suitable adhesive may be employed providing it is a biocompatible medical grade adhesive including thermoplastic and thermoset adhesives.

In some embodiments, the adhesive is a thermoset adhesive.

In some embodiments, the adhesive is an ultraviolet (UV) curable adhesive.

In one embodiment, the adhesive is a urethane-acrylic adhesive.

One example of a commercially available medical grade urethane-acrylic adhesive is Dymax® 204 CTH available from Dymax® Corporation in Torrington, Conn.

The adhesive may be applied to the balloon, the flexible circuit, or both. Suitably, the adhesive is disposed at least on the portion of the balloon and/or flexible circuit which are in contact with one another.

Additionally, bonding can be improved between the flexible circuit 22 and the balloon 20 by texturing or surface roughening of the flexible circuit 22 and/or balloon 20 prior to application of adhesive 70. This results in less delamination of the flexible circuits 22 from the balloon 20. However, it also results in higher withdrawal force compared to balloons having no texturing.

One method for texturing the surface of the balloon 20 and/or flexible circuit 22 is to create laser induced surface patterns on the surface of the flexible circuit 22 that is disposed on the balloon and/or on the outer surface of the balloon 20 to which the flexible circuit is adhered. Laser etching of the flexible circuits and/or balloon is disclosed in commonly assigned, copending U.S. patent application Ser. No. 14/316,352, the entire content of which is incorporated by reference herein.

In one embodiment, laser induced microstructures are created on both the flexible circuit 22 and the balloon 20 in patterns on the surface of each that match and create a micro latching mechanism to further reduce the chance that the flexible circuit 22 will catch and delaminate from the balloon 20 when the balloon is retracted into the catheter/sheath.

Figure 13:
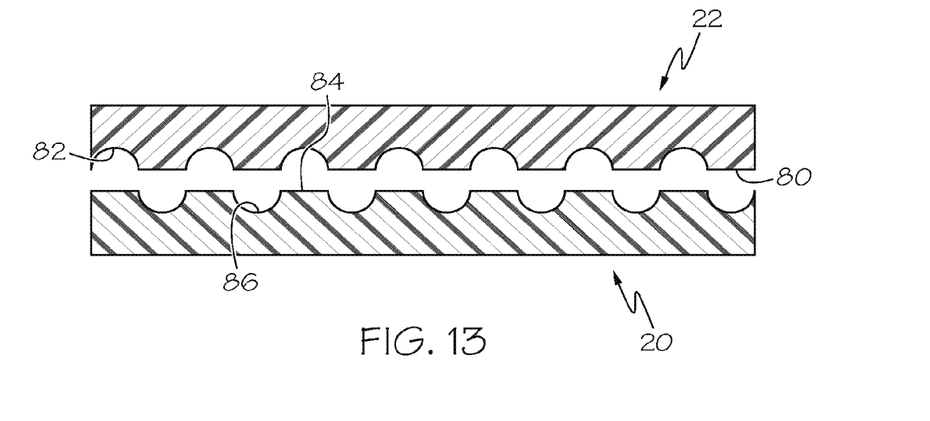
FIG. 13 is a partial view of a flexible circuit inner surface and a balloon outer surface, each having a laser induced micro pattern.

FIG. 13 is a partial view of a flexible circuit 22 having an inner surface 80 with a first laser induced micro pattern produced thereon and a balloon 20 having an outer surface 84 with a second laser induced micro pattern 86 produced thereon. Laser induced micro patterns 82, 86 are created such that the patterns match and create a micro latching system.

Figure 14:
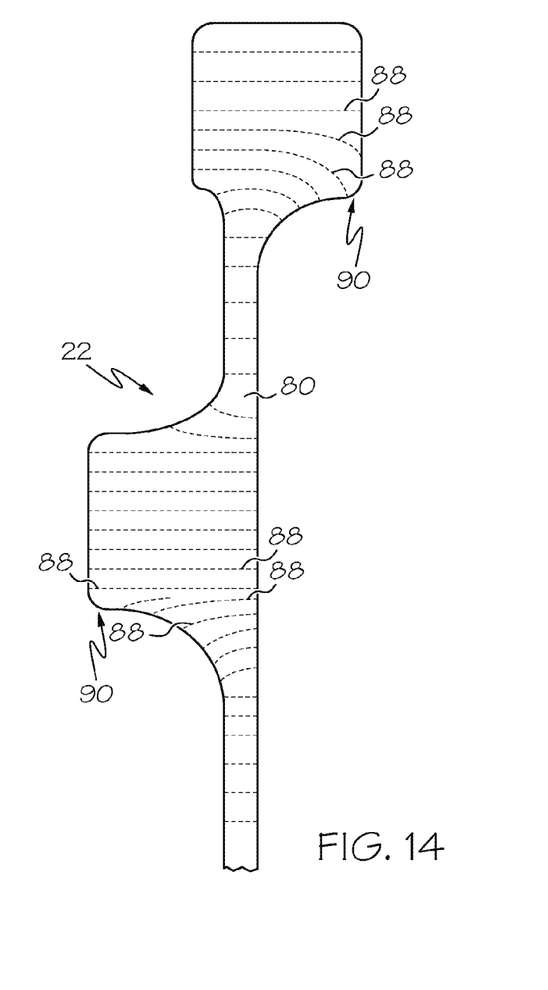
FIG. 14 is a flat view of an inner surface of a flexible circuit having another embodiment of a laser induced micro pattern created thereon.

In one embodiment, the laser induced pattern is created in a line that is perpendicular to the lifting force that is produced in the flexible circuit edge. FIG. 14 is a top down view of the inner surface 80 or back side of a flexible circuit 22 having a laser induced micro pattern 88 that is created perpendicularly to the lifting force induced on the edges of the flexible circuit 22 as shown in FIG. 14. This may include laser induced micro pattern 88 extending orthogonally across the flexible circuit (e.g. transverse to the longitudinal axis along areas where the edges of the flexible circuit 22 are parallel to the longitudinal axis of the flexible circuit 22; in a direction aligned with the radius of curvature in areas where the edges of the flexible circuit 22 are curved). The lifting force shown in FIG. 14 can occur when the balloon is pulled back into the sheath after treatment of an artery. In a typical procedure, both the left and the right renal artery are treated. The balloon is pushed from the sheath for the first treatment, inflated, and energy is applied via the electrodes to the artery. The balloon is then deflated and pulled back into the sheath to move the device to the second treatment site. The lifting force occurs on the edges indicated at reference numeral 90 of the flexible circuit as shown in FIG. 14.

In one embodiment, the flexible circuits are laser etched prior to cutting them to dyad (360 dyads per polymer sheet for up to 120 catheters, for example) which reduces the processing time and cost. Each balloon, on the other hand, is loaded onto a fixture and rotated to partially laser etch the balloon surface.

It has been found that electrode attachment robustness can be improved by texturing the outer surface of the balloon and/or the inner surface or bonding surface of the flexible circuit.

The description provided herein is not to be limited in scope by the specific embodiments described which are intended as single illustrations of individual aspects of certain embodiments. The methods, compositions and devices described herein can comprise any feature described herein either alone or in combination with any other feature(s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

U.S. Patent Application Pub. No. US 2013/0165926 is herein incorporated by reference.

U.S. patent application Ser. No. 14/070,211 is herein incorporated by reference.

U.S. Patent Application No. 61/891,257 is herein incorporated by reference.

All published documents, including all US patent documents and US patent publications, mentioned anywhere in this application are hereby expressly incorporated herein by reference in their entirety. Any copending patent applications, mentioned anywhere in this application are also hereby expressly incorporated herein by reference in their entirety. Citation or discussion of a reference herein shall not be construed as an admission that such is prior art.

What is claimed is:

1. A balloon comprising:
   a balloon wall comprising an outer surface; and
   a flexible circuit disposed on the outer surface of the balloon wall, the flexible circuit comprising a base formed of a polymer material;
   wherein the base comprises patterned deformations comprising lines;
   wherein the outer surface of the balloon wall comprises patterned deformations comprising lines, at least a portion of the lines of the outer surface of the balloon wall corresponding to at least a portion of the lines of the patterned deformations of the base; and
   wherein the patterned deformations of the base and the patterned deformations of the outer surface of the balloon wall are coupled to each other such that a remainder of the base that is not coupled to the outer surface of the balloon wall moves freely with respect to the outer surface of the balloon wall.

2. The balloon of claim 1, wherein each of the lines of the patterned deformations of the base extend across a longitudinal axis of the flexible circuit.

3. The balloon of claim 1, wherein the patterned deformations of the base and the patterned deformations of the outer surface of the balloon wall each comprise laser induced micro patterns.

4. The balloon of claim 1, wherein the lines of the patterned deformations of the base comprise lines that are substantially perpendicular to an edge of the base.

5. The balloon of claim 4, wherein the edge of the base includes at least one curve and the lines of the patterned deformations of the base include at least one end of at least one line perpendicular to the edge at the at least one curve.

6. The balloon of claim 1, wherein the flexible circuit is partially adhered to the outer surface of the balloon wall with an adhesive that occupies only portions of the base.

7. The balloon of claim 1, wherein the base of the flexible circuit comprises at least two pads and a distal spline connecting the at least two pads such that the at least two pads are spaced apart from each other.

8. A balloon comprising:
   a balloon wall comprising an outer surface; and
   a flexible circuit disposed on the outer surface of the balloon wall, the flexible circuit comprising a base formed of a polymer material;
   wherein the base comprises patterned deformations comprising lines;
   wherein the outer surface of the balloon wall comprises patterned deformations comprising lines, at least a portion of the lines of the outer surface of the balloon wall substantially matched with at least a portion of the lines of the patterned deformations of the base; and
   wherein the flexible circuit is partially adhered to the outer surface of the balloon wall with an adhesive that occupies only portions of the base.

9. The balloon of claim 4, wherein the lines of the patterned deformations of the base have ends and each of the ends is substantially perpendicular to an edge of the base.

10. The balloon of claim 9, wherein the edge of the base includes at least one curve and the lines of the patterned deformations of the base include at least one end of at least one line perpendicular to the edge at the at least one curve.

11. The balloon of claim 8, wherein each of the lines of the patterned deformations of the base extend across a longitudinal axis of the flexible circuit.

12. The balloon of claim 8, wherein the patterned deformations of the base and the patterned deformations of the outer surface of the balloon wall each comprise laser induced micro patterns.

13. The balloon of claim 8, wherein the patterned deformations of the base and the patterned deformations of the outer surface of the balloon wall are arranged such that the base is coupled to the outer surface of the balloon wall via at least a portion of the patterned deformations of the base and at least a portion of the patterned deformations of the outer surface of the balloon wall.

14. The balloon of claim 8, wherein the base of the flexible circuit comprises at least two pads and a distal spline connecting the at least two pads such that the at least two pads are spaced apart from each other.

15. A balloon comprising:
    a balloon wall comprising an outer surface; and
    a flexible circuit disposed on the outer surface of the balloon wall, the flexible circuit comprising a base formed of a polymer material;
    wherein the base comprises patterned deformations comprising lines;
    wherein the outer surface of the balloon wall comprises patterned deformations comprising lines, at least a portion of the lines of the patterned deformations of the outer surface of the balloon wall configured to interlock with at least a portion of the lines of the patterned deformations of the base; and
    wherein the flexible circuit is partially adhered to the outer surface of the balloon wall with an adhesive that occupies only portions of the base.

16. The balloon of claim 15, wherein each of the lines of the patterned deformations of the base extend across a longitudinal axis of the flexible circuit.

17. The balloon of claim 15, wherein the patterned deformations of the base and the patterned deformations of the outer surface of the balloon wall each comprise laser induced micro patterns.

18. The balloon of claim 15, wherein the patterned deformations comprising lines having ends, each end being substantially perpendicular to an edge of the base.

19. The balloon of claim 18, wherein the edge of the base includes at least one curve and the lines of the patterned deformations of the base include at least one end of at least one line perpendicular to the edge at the at least one curve.

20. The balloon of claim 15, wherein the base of the flexible circuit comprises at least two pads and a distal spline connecting the at least two pads such that the at least two pads are spaced apart from each other.

\* \* \* \* \*